United States Patent [19]

Freyne et al.

[11] Patent Number: 5,952,510
[45] Date of Patent: Sep. 14, 1999

[54] 1,3-DIHYDRO-1-(PHENYLALKENYL)-2H-IMIDAZOL-2-ONE DERIVATIVES HAVING PDE IV AND CYTOKINE INHIBITING ACTIVITY

[75] Inventors: Eddy Jean Edgard Freyne, Rumst; Gaston Stanislas Marcella Diels, Ravels, both of Belgium; José Ignacio Andrés-Gil, Madrid; Francisco Javier Fernández-Gadea, Toledo, both of Spain

[73] Assignee: Janssen Pharmaceutica, N.V., Beerse, Bulgaria

[21] Appl. No.: 08/945,849

[22] PCT Filed: Mar. 28, 1996

[86] PCT No.: PCT/EP96/01395

§ 371 Date: Sep. 30, 1997

§ 102(e) Date: Sep. 30, 1997

[87] PCT Pub. No.: WO96/31486

PCT Pub. Date: Oct. 10, 1996

[30] Foreign Application Priority Data

Apr. 6, 1995 [EP] European Pat. Off. .............. 95200869

[51] Int. Cl.⁶ ...................... C07D 233/32; C07D 233/70; A61K 31/415
[52] U.S. Cl. .................... 548/324.1; 514/398; 548/323.5
[58] Field of Search ............................ 548/323.5, 324.1; 514/398

[56] References Cited

U.S. PATENT DOCUMENTS 3,551,417  12/1970  Symon et al. .................... 548/323.5 X
5,494,927   2/1996  Cetenko et al. ........................ 514/386
5,677,464  10/1997  Itoh et al. ............................. 548/264.6

FOREIGN PATENT DOCUMENTS

WO 92/07567  5/1992  WIPO .
WO 94/12461  6/1994  WIPO .
WO 94/14800  7/1994  WIPO .
WO 94/20455  9/1994  WIPO .

Primary Examiner—Floyd D. Higel
Attorney, Agent, or Firm—Mary A. Appollina

[57] ABSTRACT

The present invention concerns the compounds of formula $$R^2O-\underset{R^1O}{\underset{|}{\bigcirc}}-\overset{R^3}{\underset{}{\bigcirc}}-\overset{R^4}{\underset{|}{C}}=\overset{R^5}{\underset{|}{C}}-Y-\overset{O}{\underset{A-B}{N\diagup\diagdown N}}-L \quad (I)$$

the N-oxide forms, the pharmaceutically acceptable acid or base addition salts and the stereochemically isomeric forms thereof, wherein $R^1$ and $R^2$ each independently are hydrogen; $C_{1-6}$alkyl; difluoromethyl; trifluoromethyl; $C_{3-6}$cycloalkyl; a saturated 5-, 6 or 7-membered heterocycle containing one or two heteroatoms selected from oxygen, sulfur or nitrogen; indanyl; bicyclo[2.2.1]-2-heptenyl; bicyclo[2.2.1]heptanyl; $C_{1-6}$alkylsulfonyl; arylsulfonyl; or substituted $C_{1-10}$alkyl; $R^3$ is hydrogen, halo or $C_{1-6}$alkyloxy; $R^4$ is hydrogen; cyano; optionally substituted $C_{1-6}$alkyl; $C_{1-6}$alkyloxycarbonyl or aryl; $R^5$ is hydrogen; cyano; optionally substituted $C_{1-6}$alkyl; $C_{1-6}$alkyloxycarbonyl or aryl; Y is a direct bond or $C_{1-3}$alkanediyl; —A—B— is a bivalent radical of formula —$CR^6$=$CR^7$— or —$CHR^6$—$CHR^7$—; L is hydrogen; optionally substituted $C_{1-6}$alkyl; $C_{1-6}$alkylcarbonyl; $C_{1-6}$alkyloxycarbonyl; $C_{1-6}$alkylsulfonyl or arylsulfonyl; aryl is optionally substituted phenyl; Het is morpholinyl or optionally substituted piperidinyl, -piperazinyl, -pyridinyl;, -furanyl or -thienyl; having PDE IV and cytokine inhibiting activity. Further, pharmaceutical compositions, preparations and use as a medicine are described.

20 Claims, No Drawings

1,3-DIHYDRO-1-(PHENYLALKENYL)-2H-IMIDAZOL-2-ONE DERIVATIVES HAVING PDE IV AND CYTOKINE INHIBITING ACTIVITY

CROSS-REFERENCE TO RELATED APPLICATIONS

This application is a National Stage application under 35 U.S.C. § 371 of PCT/EP96/01395 filed Mar. 28, 1996, which claims priority from European Application Serial No. 95.200.869.6, filed Apr. 6, 1995.

The present invention concerns 1,3dihydro1-(phenylalkenyl)-2H-imidazol-2-one derivatives having PDE IV and cytokine inhibiting activity and their preparation; it further relates to compositions comprising them, as well as their use as a medicine.

WO 94/12461, WO 94/20455 and WO 94/14800 generically disclose a number of 1-(phenylalkenyl)-2-hydroxy-imidazole derivatives as selective inhibitors of phosphodiesterase type IV (PDE IV).

Unexpectedly, particular 1,3-dihydro-1-(phenylalkenyl)-2H-imidazol-2-one derivatives show improved PDE IV inhibiting activity over the art compounds. In addition, the compounds of the present invention were found to display cytokine inhibiting activity. In view of these pharmacological properties, the present compounds have therapeutical utility in the treatment of disease states related to an abnormal enzymatic or catalytic activity of PDE IV, and/or disease states related to a physiologically detrimental excess of cytokines, in particular allergic, atopic and inflammatory diseases.

The present invention concerns 1,3-dihydro-1-(phenylalkenyl)-2H-imidazol-2-one derivatives having the formula

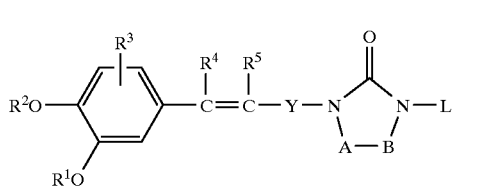

(I)

the N-oxide forms, the pharmaceutically acceptable acid or base addition salts and the stereochemically isomeric forms thereof, wherein:

$R^1$ and $R^2$ each independently are hydrogen; $C_{1-6}$alkyl; difluoromethyl; trifluoromethyl; $C_{3-6}$cycloalkyl; a saturated 5-, 6- or 7-membered heterocycle containing one or two heteroatoms selected from oxygen, sulfur or nitrogen; indanyl; bicyclo[2.2.1]-2-heptenyl; bicyclo[2.2.1]heptanyl; $C_{1-6}$alkylsulfonyl; arylsulfonyl; or $C_{1-10}$alkyl substituted with one or two substituents each independently selected from aryl, pyridinyl, thienyl, furanyl, $C_{3-7}$cycloalkyl and a saturated 5-, 6- or 7-membered heterocycle containing one or two heteroatoms selected from oxygen, sulfur or nitrogen;

$R^3$ is hydrogen, halo or $C_{1-6}$alkyloxy;

$R^4$ is hydrogen; cyano; $C_{1-6}$alkyl; $C_{1-6}$alkyloxycarbonyl; aryl or $C_{1-6}$alkyl substituted with aryl, cyano, carboxyl or $C_{1-6}$alkyloxycarbonyl;

$R^5$ is hydrogen; cyano; $C_{1-6}$alkyl; $C_{1-6}$alkyloxycarbonyl; aryl or $C_{1-6}$alkyl substituted with aryl, cyano, carboxyl or $C_{1-6}$alkyloxycarbonyl;

Y is a direct bond or $C_{1-3}$alkanediyl;

—A—B— is a bivalent radical of formula:
—$CR^6$=$CR^7$— (a-1); or
—$CHR^6$—$CHR^7$— (a-2);

wherein each $R^6$ and $R^7$ independently is hydrogen or $C_{1-4}$alkyl;

L is hydrogen; $C_{1-6}$alkyl; $C_{1-6}$alkylcarbonyl; $C_{1-6}$alkyloxycarbonyl; $C_{1-6}$alkyl substituted with one or two substituents selected from the group consisting of hydroxy, $C_{1-4}$alkyloxy, $C_{1-4}$alkyloxycarbonyl, mono- and di($C_{1-4}$alkyl)amino, aryl and Het; $C_{3-6}$alkenyl; $C_{3-6}$alkenyl substituted with aryl; piperidinyl; piperidinyl substituted with $C_{1-4}$alkyl or aryl$C_{1-4}$alkyl; $C_{1-6}$alkylsulfonyl or arylsulfonyl;

aryl is phenyl or phenyl substituted with one, two or three substituents selected from halo, hydroxy, $C_{1-4}$alkyl, $C_{1-4}$alkyloxy, $C_{3-6}$cycloalkyl, trifluoromethyl, amino, nitro, carboxyl, $C_{1-4}$alkyloxycarbonyl and $C_{1-4}$alkylcarbonylamino;

Het is morpholinyl; piperidinyl; piperidinyl substituted with $C_{1-4}$alkyl or aryl$C_{1-4}$alkyl; piperazinyl; piperazinyl substituted with $C_{1-4}$alkyl or aryl$C_{1-4}$alkyl; pyridinyl; pyridinyl substituted with $C_{1-4}$alkyl; furanyl; furanyl substituted with $C_{1-4}$alkyl; thienyl or thienyl substituted with $C_{1-4}$alkyl or $C_{1-4}$alkylcarbonylamino.

Some of the compounds of formula (I) may also exist in their tautomeric forms. Such forms although not explicitly indicated in the above formula are intended to be included within the scope of the present invention.

In $R^1$ and $R^2$, the saturated 5-, 6- or 7-membered heterocycles containing one or two heteroatoms selected from oxygen, sulfur or nitrogen may suitably be selected from heterocycles such as, for example, tetrahydrofuranyl, dioxolanyl, pyrrolidinyl, morpholinyl, piperidinyl, piperazinyl and tetrahydropyranyl. Said heterocyclic radicals are attached to the $C_{1-10}$alkyl radical by any carbon atom or, where appropriate, by a nitrogen atom.

As used in the foregoing definitions the term halo is generic to fluoro, chloro, bromo and iodo; the term $C_{1-4}$alkyl is meant to include straight chained or branched saturated hydrocarbons having from 1 to 4 carbon atoms such as, for example, methyl, ethyl, 1-methylethyl, 1,1-dimethylethyl, propyl, 2-methylpropyl and butyl; the term $C_{1-6}$alkyl is meant to include $C_{1-4}$alkyl and the higher homologues thereof having 5 to 6 carbon atoms such as, for example, 2-methylbutyl, pentyl and hexyl; the term $C_{3-6}$alkenyl defines straight and branch chained hydrocarbon radicals containing one double bond and having from 3 to 6 carbon atoms such as, for example, 2-propenyl, 3-butenyl, 2-butenyl, 2-pentenyl, 3-pentenyl, 3-methyl-2-butenyl and the like; and the carbon atom of said $C_{3-6}$alkenyl being connected to a nitrogen atom preferably is saturated; the term $C_{3-6}$cycloalkyl is generic to cyclopropyl, cyclobutyl, cyclopentyl and cyclohexyl; the term $C_{1-3}$alkanediyl is meant to include straight chained and branched saturated bivalent hydrocarbon radicals having 1 to 3 carbon atoms, such as, for example, methylene, 1,2-ethanediyl, 1,1-ethanediyl, 1,3-propanediyl, 1,2-propanediyl and 1,1-propanediyl.

The pharmaceutically acceptable acid addition salts as mentioned hereinabove are meant to comprise the acid addition salt forms which can conveniently be obtained by treating the base form of the compounds of formula (I) with appropriate acids such as inorganic acids, for example, hydrohalic acid, e.g. hydrochloric or hydrobromic, sulfuric, nitric, phosphoric and the like acids; or organic acids, such as, for example, acetic, hydroxy-acetic, propanoic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely, said acid addition salt forms can be converted in the free base forms by treatment with an appropriate base.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt also comprises the hydrates and solvent addition forms which the compounds of formula (I) are able to form. Examples of such forms are e.g. hydrates, alcoholates and the like.

The N-oxide forms of the compounds of formula (I) are meant to comprise those compounds of formula (I) wherein one or several nitrogen atoms are oxidized to the so-called N-oxide.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration. Compounds of formula (I) may occur as mixtures of E- and Z-forms or as pure E-forms or pure Z-forms.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically. The pure and mixed stereochemically isomeric forms of the compounds of formula (I) are intended to be embraced within the scope of the present invention.

An alternative manner of separating the enantiomeric forms of the compounds of formula (I) and intermediates used hereinafter involves liquid chromatography, in particular liquid chromatography using a chiral stationary phase.

Whenever used hereinafter, the term compounds of formula (I) is meant to include also the N-oxide forms, the pharmaceutically acceptable acid or base additions salts and all stereoisomeric forms.

A first set of particular groups of compounds of formula (I) consists of those wherein one or more of the following provisions apply:
  a) $R^1$ is $C_{1-6}$alkyl or $C_{3-6}$cycloalkyl and $R^2$ is $C_{1-6}$alkyl;
  b) $R^3$ is hydrogen;
  c) Y is a direct bond, methylene or 1,2-ethanediyl;
  d) L is hydrogen, $C_{1-6}$alkyl, $C_{1-6}$alkylcarbonyl or diaryl$C_{1-6}$alkyl, preferably L is hydrogen or diaryl$C_{1-6}$alkyl;
  e) —A—B— is a bivalent radical of formula (a-1), preferably a bivalent radical of formula (a-1) wherein $R^6$ and $R^7$ are both hydrogen.

A second set of particular groups of compounds of formula (I) consists of those wherein one or more of the following provisions apply:
  1) $R^1$ is hydrogen; a saturated 5-, 6- or 7-membered heterocycle containing one or two heteroatoms selected from oxygen, sulfur or nitrogen; bicyclo[2.2.1]-2-heptenyl; $C_{1-6}$alkylsulfonyl; arylsulfonyl; or $C_{1-10}$alkyl substituted with one or two substituents each independently selected from pyridinyl, thienyl, furanyl, $C_{3-7}$cycloalkyl and a saturated 5-, 6- or 7-membered heterocycle containing one or two heteroatoms selected from oxygen, sulfur or nitrogen;
  2) $R^2$ is hydrogen, $C_{3-6}$cycloalkyl; a saturated 5-, 6- or 7-membered heterocycle containing one or two heteroatoms selected from oxygen, sulfur or nitrogen; indanyl; bicyclo[2.2.1]-2-heptenyl; bicyclo[2.2.1]heptanyl; $C_{1-6}$alkylsulfonyl; arylsulfonyl; or $C_{1-10}$alkyl substituted with one or two substituents each independently selected from aryl, pyridinyl, thienyl, furanyl, $C_{3-7}$cycloalkyl and a saturated 5-, 6- or 7-membered heterocycle containing one or two heteroatoms selected from oxygen, sulfur or nitrogen;
  3) $R^3$ is halo or $C_{1-6}$alkyloxy;
  4) $R^4$ is cyano; $C_{1-6}$alkyl; aryl or $C_{1-6}$alkyl substituted with aryl, cyano, carboxyl or $C_{1-6}$alkyloxycarbonyl;
  5) $R^5$ is cyano; $C_{1-6}$alkyl; aryl or $C_{1-6}$alkyl substituted with aryl, cyano, carboxyl or $C_{1-6}$alkyloxycarbonyl;
  6) $R^4$ is cyano; $C_{1-6}$alkyl; $C_{1-6}$alkyloxycarbonyl; aryl or $C_{1-6}$alkyl substituted with aryl, cyano, carboxyl or $C_{1-6}$alkyloxycarbonyl; and $R^5$ is other than hydrogen;
  7) $R^5$ is cyano; $C_{1-6}$alkyl; $C_{1-6}$alkyloxycarbonyl; aryl or $C_{1-6}$alkyl substituted with aryl, cyano, carboxyl or $C_{1-6}$alkyloxycarbonyl; and $R^4$ is other than hydrogen;
  8) —A—B— is a bivalent radical of formula (a-2);
  9) L is $C_{1-6}$alkylcarbonyl; $C_{1-6}$alkyl substituted with hydroxy or $C_{1-4}$alkyloxy; $C_{3-6}$alkenyl; $C_{3-6}$alkenyl substituted with aryl; $C_{1-6}$alkylsulfonyl or arylsulfonyl.

An interesting subgroup within said second set of groups consists of those compounds of formula (I) wherein $R^4$ is cyano; $C_{1-6}$alkyl; aryl or $C_{1-6}$alkyl substituted with aryl, cyano, carboxyl or $C_{1-6}$alkyloxycarbonyl; or $R^5$ is cyano; $C_{1-6}$alkyl; aryl or $C_{1-6}$alkyl substituted with aryl, cyano, carboxyl or $C_{1-6}$alkyloxycarbonyl.

Another interesting subgroup within said second set of groups consists of those compounds of formula (I) wherein $R^1$ is hydrogen; a saturated 5-, 6- or 7-membered heterocycle containing one or two heteroatoms selected from oxygen, sulfur or nitrogen; bicyclo[2.2.1]-2-heptenyl; $C_{1-6}$alkylsulfonyl; arylsulfonyl; or $C_{1-10}$alkyl substituted with one or two substituents each independently selected from pyridinyl, thienyl, furanyl, $C_{3-7}$cycloalkyl and a saturated 5-, 6- or 7-membered heterocycle containing one or two heteroatoms selected from oxygen, sulfur or nitrogen.

A third set of particular groups of compounds of formula (I) consists of those wherein one or more of the following provisions apply:
1) $R^1$ is hydrogen; $C_{1-6}$alkyl; difluoromethyl; trifluoromethyl; a saturated 5-, 6- or 7-membered heterocycle containing one or two heteroatoms selected from oxygen, sulfur or nitrogen; indanyl; bicyclo[2.2.1]-2-heptenyl; bicyclo[2.2.1]heptanyl; $C_{1-6}$alkylsulfonyl; arylsulfonyl; or $C_{1-10}$alkyl substituted with one or two substituents each independently selected from aryl, pyridinyl, thienyl, furanyl, $C_{3-7}$cycloalkyl and a saturated 5-, 6- or 7-membered heterocycle containing one or two heteroatoms selected from oxygen, sulfur or nitrogen;
2) $R^2$ is hydrogen; $C_{3-6}$cycloalkyl; a saturated 5-, 6- or 7-membered heterocycle containing one or two heteroatoms selected from oxygen, sulfur or nitrogen; indanyl; bicyclo[2.2.1]-2-heptenyl; bicyclo[2.2.1]heptanyl; $C_{1-6}$alkylsulfonyl; arylsulfonyl; or $C_{1-10}$alkyl substituted with one or two substituents each independently selected from aryl, pyridinyl, thienyl, furanyl, $C_{3-7}$cycloalkyl and a saturated 5-, 6- or 7-membered heterocycle containing one or two heteroatoms selected from oxygen, sulfur or nitrogen;
3) $R^3$ is halo or $C_{1-6}$alkyloxy;
4) $R^4$ is aryl or $C_{1-6}$alkyl substituted with aryl, cyano, carboxyl or $C_{1-6}$alkyloxycarbonyl;
5) $R^5$ is aryl or $C_{1-6}$alkyl substituted with aryl, cyano, carboxyl or $C_{1-6}$alkyloxycarbonyl;
6) —A—B— is a bivalent radical of formula (a-2).

An interesting subgroup within said third set of groups consists of those compounds of formula (I) wherein $R^4$ is aryl or $C_{1-6}$alkyl substituted with aryl, cyano, carboxyl or $C_{1-6}$alkyloxycarbonyl; or $R^5$ is aryl or $C_{1-6}$alkyl substituted with aryl, cyano, carboxyl or $C_{1-6}$alkyloxycarbonyl.

Another interesting subgroup within said third set of groups consists of those compounds of formula (I) wherein $R^1$ is hydrogen; $C_{1-6}$alkyl; difluoromethyl; trifluoromethyl; a saturated 5-, 6- or 7-membered heterocycle containing one or two heteroatoms selected from oxygen, sulfur or nitrogen; indanyl; bicyclo[2.2.1]-2-heptenyl; bicyclo[2.2.1]heptanyl; $C_{1-6}$alkylsulfonyl; arylsulfonyl; or $C_{1-10}$alkyl substituted with one or two substituents each independently selected from aryl, pyridinyl, thienyl, furanyl, $C_{3-7}$cycloalkyl and a saturated 5-, 6- or 7-membered heterocycle containing one or two heteroatoms selected from oxygen, sulfur or nitrogen.

A fourth set of particular groups of compounds of formula (I) consists of those wherein one or more of the following provisions apply:
1) $R^1$ is hydrogen; a saturated 5-, 6- or 7-membered heterocycle containing one or two heteroatoms selected from oxygen, sulfur or nitrogen; indanyl; bicyclo[2.2.1]-2-heptenyl; bicyclo[2.2.1]heptanyl; $C_{1-6}$alkylsulfonyl; arylsulfonyl; or $C_{1-10}$alkyl substituted with one or two substituents each independently selected from aryl, pyridinyl, thienyl, furanyl, $C_{3-7}$cycloalkyl and a saturated 5-, 6- or 7-membered heterocycle containing one or two heteroatoms selected from oxygen, sulfur or nitrogen;
2) $R^2$ is hydrogen; $C_{3-6}$cycloalkyl; a saturated 5-, 6- or 7-membered heterocycle containing one or two heteroatoms selected from oxygen, sulfur or nitrogen; indanyl; bicyclo[2.2.1]-2-heptenyl; bicyclo[2.2.1]heptanyl; $C_{1-6}$alkylsulfonyl; arylsulfonyl; or $C_{1-10}$alkyl substituted with one or two substituents each independently selected from aryl, pyridinyl, thienyl, furanyl, $C_{3-7}$cycloalkyl and a saturated 5-, 6- or 7-membered heterocycle containing one or two heteroatoms selected from oxygen, sulfur or nitrogen;
3) $R^3$ is halo or $C_{1-6}$alkyloxy;
4) $R^4$ is hydrogen; cyano; $C_{1-6}$alkyl; $C_{1-6}$alkyloxycarbonyl or $C_{1-6}$alkyl substituted with cyano, carboxyl or $C_{1-6}$alkyloxycarbonyl;
5) $R^5$ is hydrogen; cyano; $C_{1-6}$alkyl; $C_{1-6}$alkyloxycarbonyl or $C_{1-6}$alkyl substituted with cyano, carboxyl or $C_{1-6}$alkyloxycarbonyl;
6) —A—B— is a bivalent radical of formula (a-2).

An interesting subgroup within said fourth set of groups consists of those compounds of formula (I) wherein $R^4$ is hydrogen; cyano; $C_{1-6}$alkyl; $C_{1-6}$alkyloxycarbonyl or $C_{1-6}$alkyl substituted with cyano, carboxyl or $C_{1-6}$alkyloxycarbonyl; or $R^5$ is hydrogen; cyano; $C_{1-6}$alkyl; $C_{1-6}$alkyloxycarbonyl or $C_{1-6}$alkyl substituted with cyano, carboxyl or $C_{1-6}$alkyloxycarbonyl.

Another interesting subgroup within said fourth set of groups consists of those compounds of formula (I) wherein $R^1$ is hydrogen; a saturated 5-, 6- or 7-membered heterocycle containing one or two heteroatoms selected from oxygen, sulfur or nitrogen; indanyl; bicyclo[2.2.1]-2-heptenyl; bicyclo[2.2.1]heptanyl; $C_{1-6}$alkylsulfonyl; arylsulfonyl; or $C_{1-10}$alkyl substituted with one or two substituents each independently selected from aryl, pyridinyl, thienyl, furanyl, $C_{3-7}$cycloalkyl and a saturated 5-, 6- or 7-membered heterocycle containing one or two heteroatoms selected from oxygen, sulfur or nitrogen.

Preferred compounds are those compounds of formula (I) wherein $R^4$ is $C_{1-6}$alkyl substituted with cyano, carboxyl or $C_{1-6}$alkyloxycarbonyl; or $R^5$ is $C_{1-6}$alkyl substituted with cyano, carboxyl or $C_{1-6}$alkyloxycarbonyl.

Also preferred compounds are those compounds of formula (I) wherein $R^1$ is hydrogen; a saturated 5-, 6- or 7-membered heterocycle containing one or two heteroatoms selected from oxygen, sulfur or nitrogen; bicyclo[2.2.1]-2-heptenyl; $C_{1-6}$alkylsulfonyl; arylsulfonyl; or $C_{1-10}$alkyl substituted with one or two substituents each independently selected from pyridinyl, thienyl, furanyl, $C_{3-7}$cycloalkyl and a saturated 5-, 6- or 7-membered heterocycle containing one or two heteroatoms selected from oxygen, sulfur or nitrogen.

Most preferred are the compounds:
1-[2-[3-(cyclopentyloxy)-4-methoxyphenyl]-2-phenylethenyl]-1,3-dihydro-2H-imidazol-2-one;
ethyl 3-(cyclopentyloxy)-β-[(2,3-dihydro-2-oxo-1H-imidazol-1-yl)methylene]-4-methoxybenzenepropanoate;
1-[2-[3-(cyclopentyloxy)-4-methoxyphenyl]-1-propenyl]-3-(diphenylmethyl)-2H-imidazol-2-one;
their N-oxide forms, their pharmaceutically acceptable acid or base addition salts and their stereoisomeric forms.

Whenever used hereinafter, $R^1$ to $R^7$, Y, —A—B— and L are defined as under formula (I) unless otherwise indicated.

Compounds of formula (I) can generally be prepared by dehydrating an intermediate of formula (II) using art-known dehydration techniques.

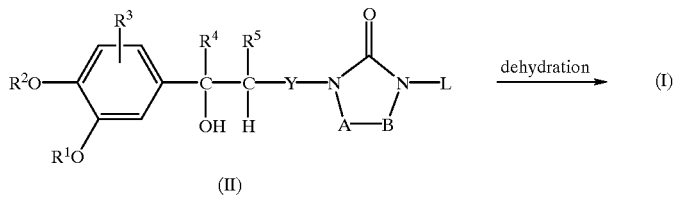

(II)

For instance, said dehydration may be performed in a reaction-inert solvent and in the presence of an acid such as, for example, hydrochloric acid or p-toluenesulfonic acid. Said dehydration may also be performed in a reaction-inert solvent such as, for example, dichloromethane, and in the presence of for example mesylchloride or a functional derivative thereof, and in the presence of a base such as, for example, diethylethanamine. Stirring and elevated temperatures may enhance the rate of the reaction.

In this and the following preparations, the reaction products may be isolated from the reaction medium and, if necessary, further purified according to methodologies generally known in the art such as, for example, extraction, crystallization, trituration and chromatography.

Compounds of formula (I) wherein L is other than hydrogen, said L being represented by L' and said compounds being represented by formula (I-a), may be prepared by reacting an intermediate of formula (III) with a Wittig reagent of formula (IV-a) wherein X is a suitable counter ion such as, for example, a halogen, in a reaction-inert solvent and in the presence of a suitable base such as, for example, butyllithium or sodium hydride. The phosphonium salt-type intermediates of formula (IV-a) may be replaced by the more reactive phosphonic ester-type intermediates of formula (IV-a).

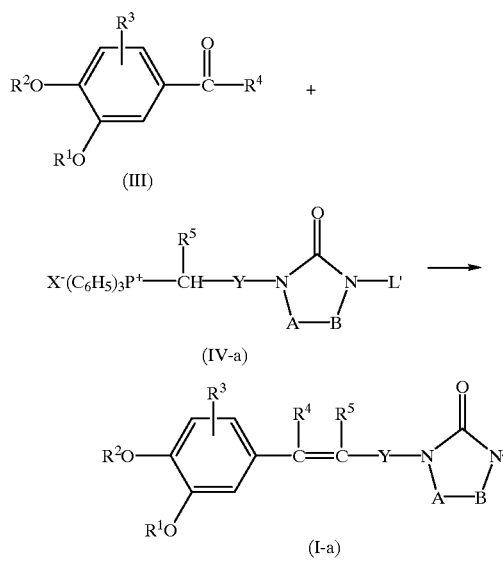

Compounds of formula (I) wherein L is hydrogen, said compounds being represented by formula (I-b), may be obtained by using an intermediate of formula (IV-b) wherein G is a suitable protecting group, in the above mentioned reaction, and subsequently deprotecting the thus obtained intermediate following art-known deprotection techniques.

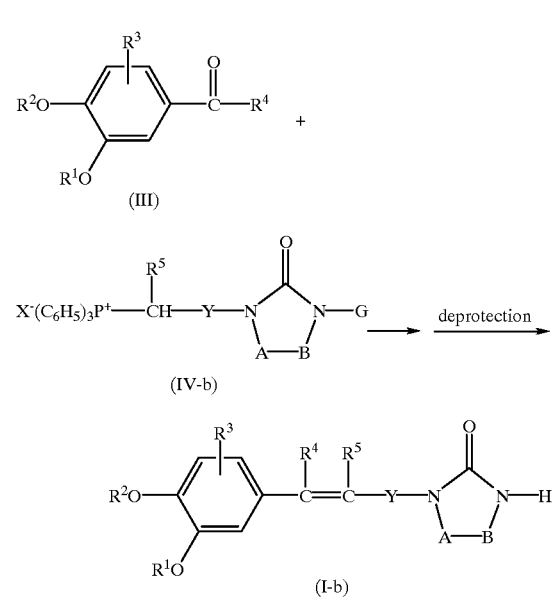

Compounds of formula (I-a) wherein Y is restricted to $C_{1-3}$alkanediyl, said Y being represented by Y' and said compounds being represented by (I-a-1), may be prepared by reacting a Wittig reagent of formula (V) with an intermediate of formula (VI-a) in a reaction-inert solvent and in the presence of a base such as, for example, butyllithium or sodium hydride. The phosphonium salt-type intermediates of formula (VI-a) may be replaced by the more reactive phosphonic ester-type intermediates of formula (VI-a).

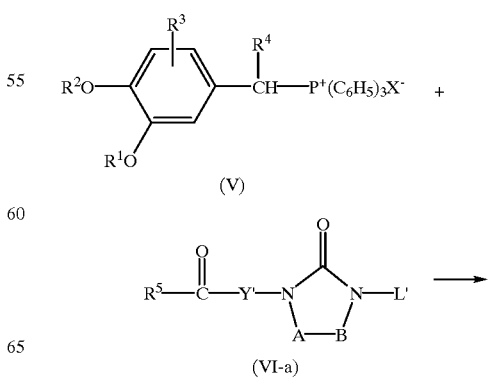

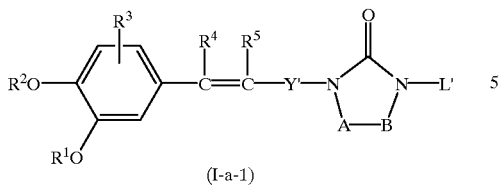

(I-a-1)

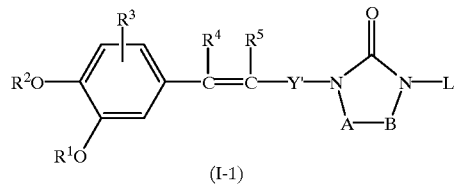

(I-1)

Compounds of formula (I-b) wherein Y is Y', said compounds being represented by formula (I-b-1), may be obtained by using an intermediate of formula (VI-b) wherein G is a suitable protecting group, in the above mentioned reaction, and subsequently deprotecting the thus obtained intermediate following art-known deprotection techniques.

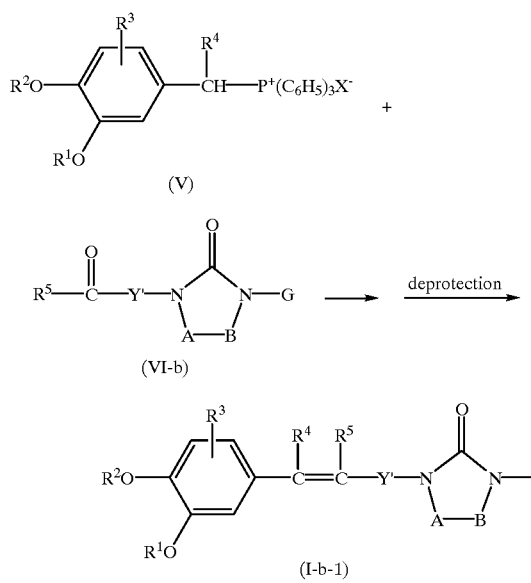

Compounds of formula (I) wherein Y is Y', said compounds being represented by formula (I-1), may be prepared by N-alkylating a 1,3dihydro-2H-imidazol-2-one derivative of formula (VIII), with an intermediate of formula (VII) wherein $W^1$ is a reactive leaving group such as, for example, a halogen.

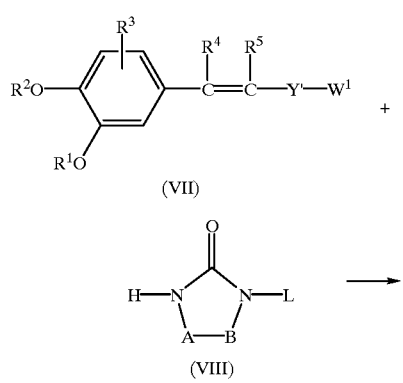

Said N-alkylation may conveniently be performed in the presence of a base such as, for example, butyllithium, sodium hydride or sodium bis(trimethylsilyl)amide, in a reaction-inert solvent such as, for example, tetrahydrofuran, optionally cooled on an ice-bath. The reaction is preferably performed under a reaction inert atmosphere such as, for example, oxygen free nitrogen. It may be advantageous to add to the reaction mixture a crown ether, e.g. 1,4,7,10,13,16-hexaoxacyclooctadecane and the like or a complexing agent such as for example, tris[2-(2-methoxyethoxy)]ethanamine and the like. Stirring may enhance the rate of the reaction.

Alternatively, compounds of formula (I-1) may be prepared by reacting an organometallic intermediate of formula (IX), wherein M is an appropriate metal ion or metalcomplex ion such as, for example, $Li^+$, $(MgBr)^+$, $B(OH)_2^+$ or $Sn(CH_3)_3^+$, and with a suitable 1,3-dihydro-2H-imidazol-2-one derivative of formula (X) wherein $W_2$ is a reactive leaving group such as, for example, a halogen.

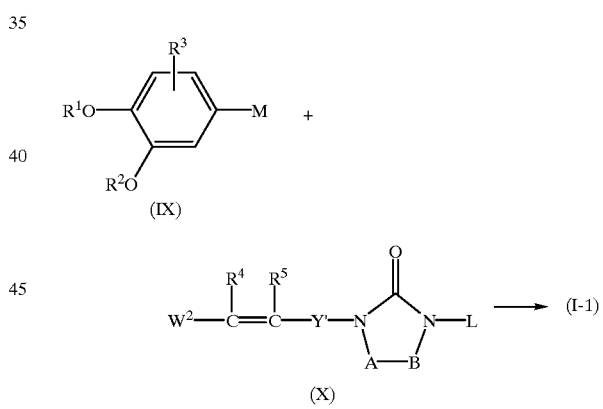

Said reaction may be performed as described in J. Mod. Chem., 37(11), 1550 (1994).

Compounds of formula (1-b-1) wherein —A—B— is a radical of formula (c-1), said compounds being represented by formula (1-b-1-1), can conveniently be prepared by cyclization of an intermediate of formula (XI) or a functional derivative thereof, in the presence of a suitable acid such as, for example, hydrochloric acid.

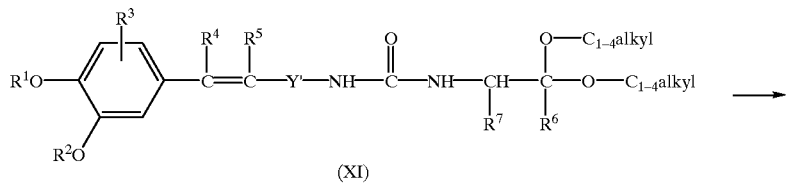

(XI)

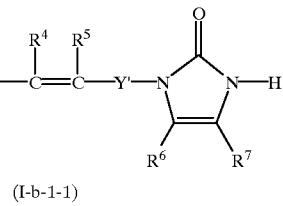

(I-b-1-1)

Said cyclization may be performed in a reaction inert solvent such as, for example, water, methanol or a mixture thereof. Stirring and heating may enhance the rate of the reaction.

Compounds of formula (I-b-1-1) may also be prepared by cyclization of an intermediate of formula (XII) or a functional derivative thereof in the presence of a suitable isocyanate, such as, for example, potassium isocyanate or trimethylsilyl isocyanate.

Compounds of formula (I-b-1) wherein —A—B— is a radical of formula (a-2), said compounds being represented by formula (I-b-1-2), can be obtained by cyclization of an intermediate of formula (XIII) or a functional derivative thereof in a reaction-inert solvent and in the presence of a suitable reagent such as, for example, phosgene, ureum or N,N'-carbonyldiimidazole.

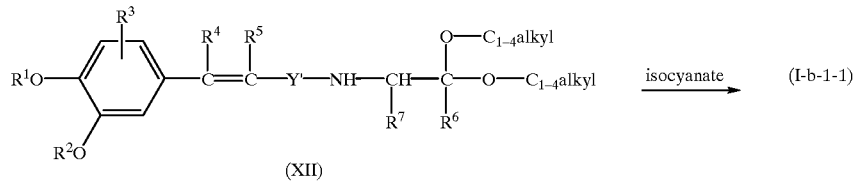

Alternatively, compounds of formula (1-b-1-1) may also be prepared by reacting an intermediate of formula (XII) with a suitable cyanide such as, for example, potassium cyanide, thus obtaining the corresponding N-cyanide derivative which may be further hydrolyzed in the presence of an acid such as, for example, hydrochloric acid, keeping the pH of the reaction mixture basic. The thus formed corresponding ureum derivative is then further cyclized in the presence of an excess of an acid such as, for example, hydrochloric acid, to a compound of formula (1-b-1-1).

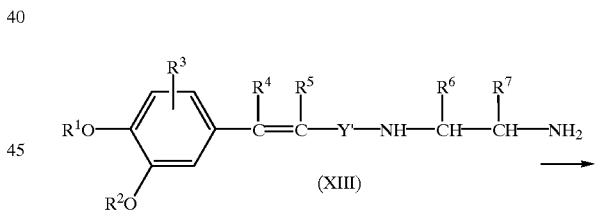

(XIII)

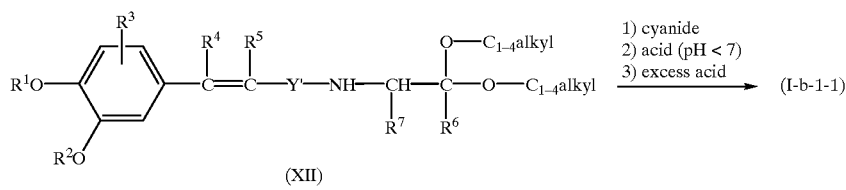

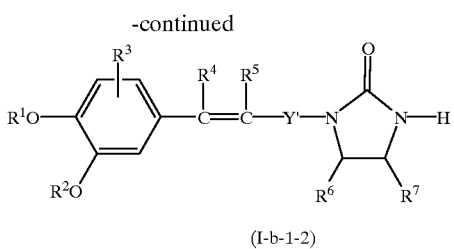

(I-b-1-2)

The compounds of formula (I) can also be converted into each other following art-known procedures of functional group transformation.

For example, compounds of formula (I-a) may be prepared by reacting a compound of formula (I-b) with L'-W³ (XIV), wherein W³ is a reactive leaving group such as, for example, a halogen atom.

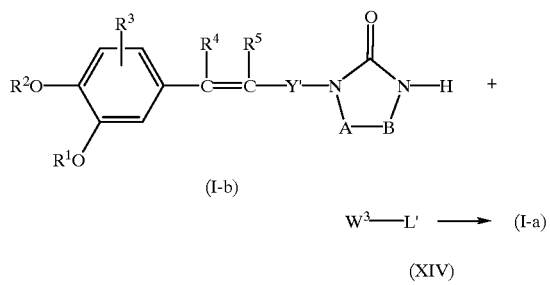

(I-b)

W³—L'  ⟶  (I-a)

(XIV)

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with 3-phenyl-2-(phenylsulfonyl)oxaziridine or with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Intermediates of formula (II) may be prepared following art-known techniques. For instance, intermediates of formula (II) may be prepared by reacting an intermediate of formula (XV) with R⁴—M (XVI) wherein M is a metal ion or a metalcomplex ion such as, for example, Li⁺ or (MgBr)⁺ in a reaction-inert solvent such as, for example, tetrahydrofuran. Said reaction may optionally be performed in an inert atmosphere such as, for example, oxygen free nitrogen.

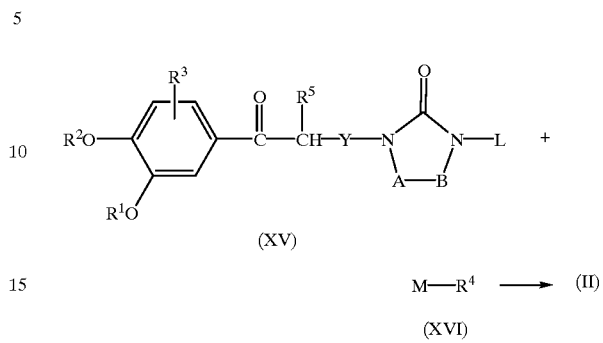

Intermediates of formula (XV) may be prepared by reacting an intermediate of formula (XVII) with an 1,3-dihydro-2H-imidazol-2-one derivative of formula (VIII) in a manner analogous to the preparation of compounds of formula (I-1) starting from the intermediates (VII) and (VIII).

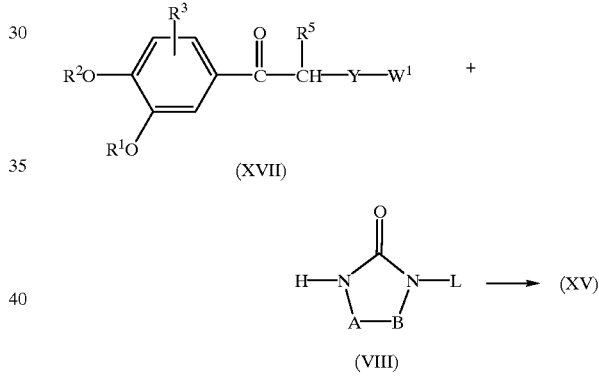

Intermediates of formula (XV) wherein —A—B— is a radical of formula (a-1), said intermediates being represented by formula (XV-1), may be prepared by cyclizing an intermediate of formula (XVIII) in a manner analogous to the preparation of a compound of formula (I-b-1-1) starting from an intermediate of formula (XI) as described hereinabove.

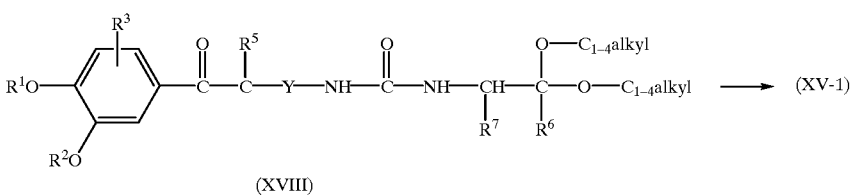

(XVIII)

Alternatively, intermediates of formula (XV-1) may be prepared by cyclizing an intermediate of formula (XIX) in a manner analogous to the preparation of a compound of formula (I-b-1-1) starting from an intermediate of formula (XIII) as described hereinabove.

Also, intermediates of formula (XVIII) may be directly formed by reacting an intermediate of formula (XXI) with a suitable reagent such as, for example, 2,2-(diC$_{1-4}$alkyloxy)ethanisocyanate, phenyl [2,2-di(C$_{1-6}$alkyloxy)ethyl] carbamate or a functional derivative of any one of said reagents.

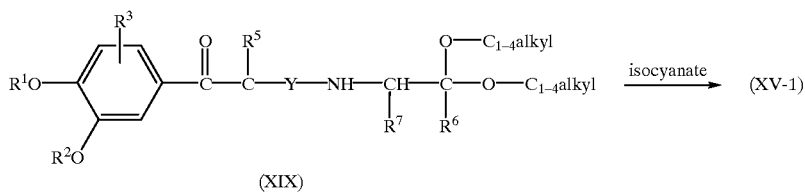

(XIX) → (XV-1) [isocyanate]

Intermediates of formula (XV) wherein —A—B— is a radical of formula (a-2), said intermediates being represented by formula (XV-2), may be prepared by cyclizing an intermediate of formula (XX) in an analogous manner to the preparation of the compounds of formula (I-b-1-2) as described hereinabove.

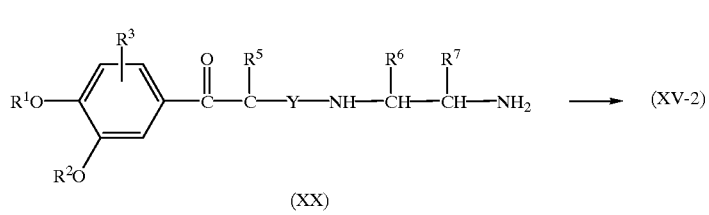

(XX) → (XV-2)

In particular, intermediates of formula (XVIII) may be prepared by first N-acylating an amine of formula (XXI) with phenyl chloroformate or a functional derivative thereof. Said N-acylation can conveniently be performed in a reaction inert solvent such as, for example, dichloromethane, benzene or toluene, optionally cooled on an ice-bath, and in the presence of a base such as, for example, N,N-diethylethanamine or sodium-bicarbonate. The thus obtained intermediate may be subsequently reacted with 2,2-(di-C$_{1-4}$alkyloxy)ethanamine or a functional derivative thereof, to form an intermediate of formula (VI). Said reaction can conveniently be performed in a reaction inert solvent such as, for example, 1,4-dioxane, in the presence of a base such as, for example, N,N-diethylethanamine, and optionally in the presence of a catalyst such as, for example, N,N-dimethyl-pyridinamine. Stirring and elevated temperatures may enhance the rate of the reaction.

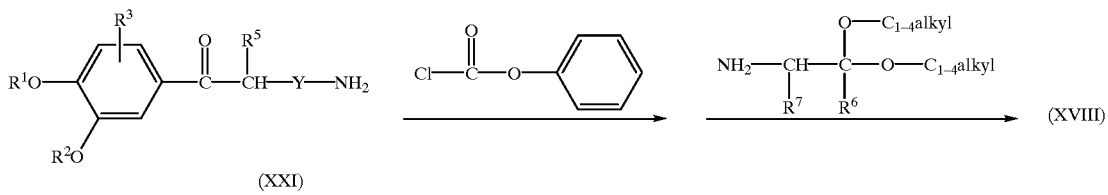

(XXI) → (XVIII)

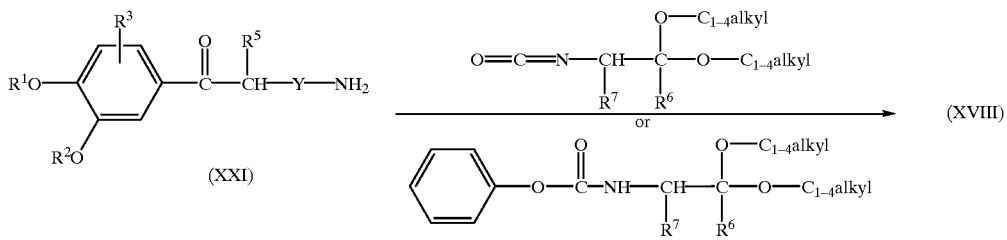

(XVIII)

Intermediates of formula (XIX) can be prepared by reacting an amine of formula (XXI) with an intermediate of formula (XXII) wherein $W^4$ is a reactive leaving group such as, for example, a halogen.

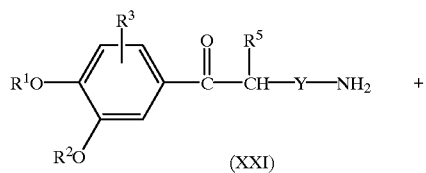

Intermediates of formula (XXI) may be prepared following art-known procedures. Some of the intermediates of formula (XXI) and their preparations are described in WO 92/00968, WO 93/15044 and WO 93/15045.

Also intermediates of formula (II) wherein $R^5$ is hydrogen, Y is a direct bond and L is hydrogen, said intermediates being represented by formula (II-a), may be prepared following the reaction process as depicted in scheme 1.

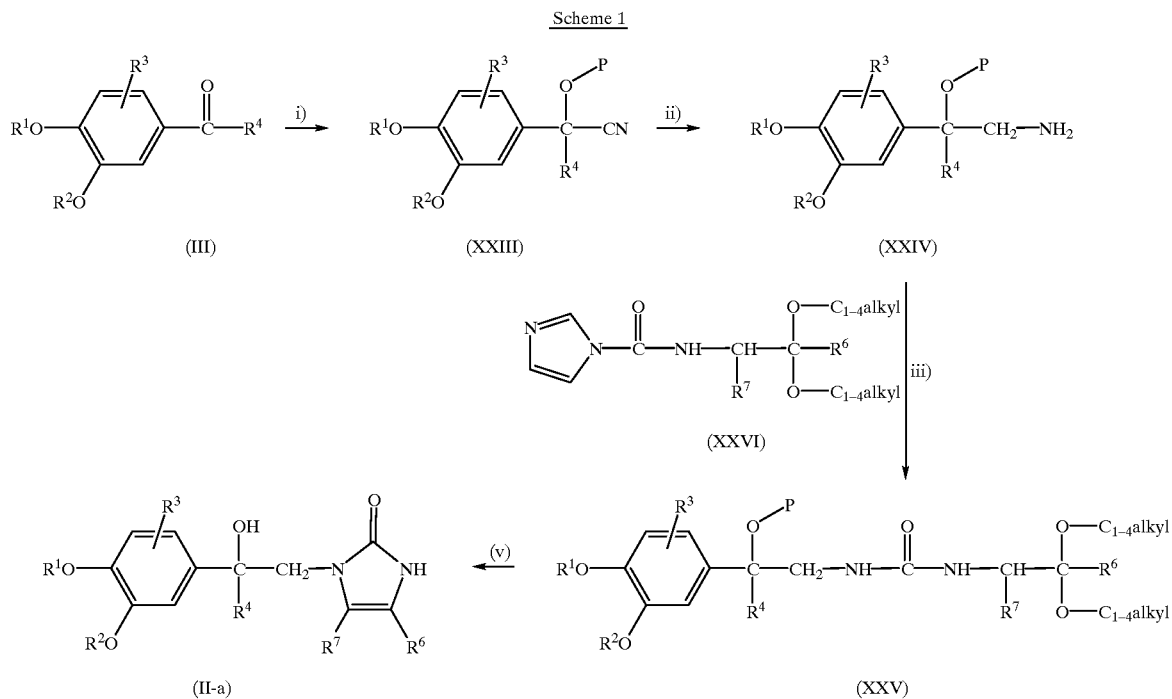

-continued

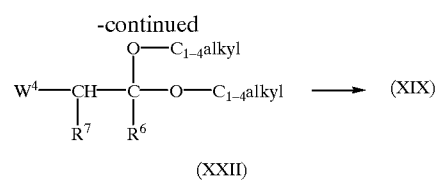

Step i) in scheme 1 involves the reaction of an intermediate of formula (III) with trimethylsilyl cyanide or a functional derivative thereof in the presence of a suitable catalyst such as, for example, zinc iodide, and in a reaction-inert solvent such as, for example, dichloromethane; thus forming an intermediate of formula (XXIII) wherein P is a trimethylsilyl protecting group or a functional derivative thereof. Depending on the nature of the $R^1$ to $R^4$ variables, P may also be hydrogen. Subsequently, in step ii), the nitrile derivative of formula (XXIII) may be reduced to the corresponding amine of formula (XXIV) using art-known techniques such as, for example, reduction with hydrogen in the presence of a suitable catalyst such as, for example, Raney nickel. Further, in step iii), intermediates of formula (XXV) may be prepared from intermediates of formula (XXIV) according to the procedures described hereinabove for the preparation of intermediates of formula (XVIII). An alternative for said procedures is the reaction of an intermediate of formula (XXIV) with an imidazole derivative of formula (XXVI) in a reaction-inert solvent such as, for example, tetrahydrofuran, preferably a temperature ranging between room temperature and reflux temperature. Finally, step iv) involves the cyclization of an intermediate of formula (XXV) to an intermediate of formula (II-a) in a manner analogous to the one described for the preparation of an intermediate of formula (XV-1) from an intermediate of formula (XVIII).

The compounds of formula (I), the N-oxide forms, the pharmaceutically acceptable acid or base addition salts and the stereochemically isomeric forms thereof, are potent inhibitors of the phosphodiesterase (PDE) isoenzymes of family IV (cAMP-specific family).

cAMP (adenosine cyclic 3', 5'-monophosphate) is a key second messenger, the concentration of which affects particular cell activities through activation of enzymes such as kinases. PDE IV is known to hydrolyse cAMP to its corresponding inactive 5'-monophosphate metabolite. Hence, inhibition of PDE IV leads to an elevation of cAMP levels in particular cells such as the respiratory smooth muscle cell and in a wide variety of inflammatory cells, i.e. certain lymphocytes, e.g. basophils, neutrophils and eosinophils, monocytes and mast-cells. A number of allergic, atopic and inflammatory diseases are deemed to be caused by higher-than-normal PDE IV concentrations which result in low cAMP levels and hypersensitivity of the thus affected cells for excitatory stimuli. (Examples of said hypersensitivity are for example, excessive histamine release from basophils and mast cells or excessive superoxide anion radical formation by eosinophils.) Hence, the present compounds having potent phosphodiesterase IV inhibitory properties are deemed useful agents in alleviating and/or curing allergic, atopic and inflammatory diseases. The functional effects of PDE IV inhibitors are e.g. respiratory smooth muscle relaxation, bronchodilation, platelet aggregation inhibition and inhibition of white blood cell mediator release. Examples of allergic diseases are bronchial asthma, cheilitis, conjunctivitis, contact dermatitis and eczema, irritable bowel disease, deshydroform eczema, urticaria, vasculitis, vulvitis; examples of atopic diseases are dermatitis and eczema, winterfeet, asthma, allergic rhinitis; and related afflictions are, for example, psoriasis and other hyperproliferative diseases.

The present invention thus also relates to compounds of formula (I) as defined hereinabove for use as a medicine, in particular for use as an anti-asthmatic medicine or as a medicine for treating atopic diseases. Thus the compounds of the present invention may be used for the manufacture of a medicament for treating asthmatic or atopic diseases, more in particular atopic dermatitis.

The PDE IV inhibitory activity of the compounds of formula (I) may be demonstrated in the test "Inhibition of recombinant human mononuclear lymphocyte (MNL) phospho-diesterase type IV B produced in insect cells with a baculovirus vector". Several in vivo and in vitro tests may be used to demonstrate the usefulness of the compounds of formula (I) in treating the described allergic, atopic and inflammatory diseases. Such tests are for instance, "Bronchoconstriction of the guinea pig trachea in vitro", "Bronchoconstriction of the guinea pig trachea in vivo" and the in vivo test "Dextran-induced oedema formation in mouse ear".

Further, the present compounds have only very low inhibitory activity on the phosphodiesterase isoenzymes of family III (cGMP-inhibited family). Inhibition of, in particular, PDE III leads to an elevation of cAMP in the cardiac muscle, thereby causing effects on the contractile force of the heart as well as on the relaxation of the heart In the treatment of the described allergic, atopic and inflammatory diseases, cardiovascular effects clearly are undesired. Hence, as the present compounds inhibit PDE IV at much lower concentrations as they inhibit PDE III, their therapeutic use may be adjusted to avoid cardiovascular side-effects.

Art-known PDE IV inhibitors often cause adverse gastrointestinal side effects. Most of the present compounds, however, have few effects on the gastro-intestinal tract, which may be demonstrated in the test "Gastric emptying of a caloric meal in rats".

The designation PDE III and IV as used herein refers to the classification by J. A. Beavo and D. H. Reifsnyder, TIPS Reviews, April 1990, pp. 150–155.

The compounds of the present invention also have cytokine inhibitory activity. A cytokine is any secreted polypeptide that affects the function of other cells by modulating interactions between cells in the immune or inflammatory response. Examples of cytokines are monokines and lymphokines and they may be produced by a wide variety of cells. For instance, a monokine is generally referred to as being produced and secreted by a mononuclear cell, such as a macrophage and/or monocyte but many other cells produce monokines, such as natural killer cells, fibroblasts, basophils, neutrophils, endothelial cells, brain astrocytes, bone marrow stromal cells, epideral keratinocytes, and β-lymphocytes. Lymphokines are generally referred to as being produced by lymphocyte cells. Examples of cytokines include Interleukin-1 (IL-1), Interleukin-2 (IL-2), Interleukin-6 (IL-6), Interleukin-8 (IL-8), alpha-Tumor Necrosis Factor (αTNF) and beta-Tumor Necrosis Factor (βTNF).

The cytokine specifically desired to be inhibited is αTNF. Excessive or unregulated TNF production is implicated in mediating or exacerbating a number of diseases including rheumatoid arthritis, rheumatoid spondylitis, osteoarthritis, gouty arthritis, and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft versus host reaction, allograft rejections, fever and myalgias due to infection, such as influenza, cachexia secondary to infection or malignancy, cachexia secondary to acquired immune deficiency syndrome (AIDS), AIDS, ARC (AIDS related complex), keloid formation, scar tissue formation, Crohn's disease, ulcerative colitis, or pyresis.

The cytokine inhibitory activity of the compounds of formula (I), such as the inhibition of αTNF production, may be demonstrated in the in vitro test "Cytokine production in human whole blood cultures".

In addition, the compounds of the present invention are expected to show no or little endocrinological side-effects. This may be evidenced by, for instance, the "Testosterone in vivo" test, the "In vitro inhibition of the aromatase activity"-test and the "In vivo inhibition of the aromatase activity"-test.

In view of their useful PDE IV and cytokine inhibiting properties, the subject compounds may be formulated into various pharmaceutical forms for administration purposes. To prepare the pharmaceutical compositions of this invention, an effective amount of the particular compound, in base or acid addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, topically, percutaneously, by inhalation or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. As appropriate compositions for topical application there may be cited all compositions usually employed for topically administering drugs e.g. creams, gellies, dressings, shampoos, tinctures, pastes, ointments, salves, powders and the like. Application of said compositions may be by aerosol, e.g. with a propellent such as nitrogen, carbon dioxide, a freon, or without a propellent such as a pump spray, drops, lotions, or a semisolid such as a thickened composition which can be applied by a swab. In particular, semisolid compositions such as salves, creams, gellies, ointments and the like will conveniently be used.

In order to enhance the solubility and/or the stability of the compounds of formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin. Also co-solvents such as alcohols may improve the solubility and/or the stability of the compounds of formula (I) in pharmaceutical compositions. In the preparation of aqueous compositions, addition salts of the subject compounds are obviously more suitable due to their increased water solubility.

It is especially advantageous to formulate the aforementioned pharmaceutical compositions in dosage unit form for ease of administration and uniformity of dosage. Dosage unit form refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions and the like, and segregated multiples thereof.

The present invention also relates to a method of treating warm-blooded animals suffering from disease states related to an abnormal enzymatic or catalytic activity of PDE IV, and/or disease states related to a physiologically detrimental excess of cytokines, in particular allergic, atopic and inflammatory diseases, more in particular asthmatic and atopic diseases, most particular atopic dermatitis. Said method comprises the administration of a therapeutically effective amount of a compound of formula (I) or a N-oxide form, a pharmaceutically acceptable acid or base addition salt or a stereochemically isomeric form thereof in admixture with a pharmaceutical carrier.

In general it is contemplated that an effective daily amount would be from 0.01 mg/kg to 10 mg/kg body weight, more preferably from 0.04 mg/kg to 5 mg/kg body weight. It is evident that said effective daily amount may be lowered or increased depending on the response of the treated subject and/or depending on the evaluation of the physician prescribing the compounds of the instant invention. The effective daily amount ranges mentioned hereinabove are therefore guidelines only and are not intended to limit the scope or use of the invention to any extent.

The following examples are intended to illustrate and not to limit the scope of the present invention.

Experimental part

Compounds of formula (I) and some intermediates have a stereogenic center. In those cases where the racemate was separated into its enantiomers, the stereochemically isomeric form which was first isolated was designated as "A" and the second as "B", without further reference to the actual stereochemical configuration.

Hereinafter, "THF" means tetrahydrofuran, "RT" means room temperature and "DIPE" means diisopropyl ether.

A. Preparation of the intermediates

EXAMPLE A.1 a) Under a $N_2$ flow, a solution of benzyltrimethylammonium dichloroiodate (78 g) in THF (250 ml) was added to a mixture of 1-[3-(cyclopentyloxy)-4-methoxyphenyl]-ethanone (26.3 g) in THF (250 ml) while stirring. The resulting reaction mixture was stirred for 16 hours at RT. The solvent was evaporated and the residue was redissolved in diethyl ether (300 ml). The mixture was added dropwise to a 5% $Na_2SO_4$ solution (400 ml). The aqueous layer was extracted twice with diethyl ether (100 ml). The combined organic layers were washed twice with water (500 ml), dried over $MgSO_4$, filtered and the solvent evaporated. The crude oil was crystallized from hexane. The precipitate was filtered off, washed with hexane and dried, yielding 11 g of 2-chloro-1-[3-(cyclopentyloxy)-4-methoxyphenyl]ethanone. The filtrate was evaporated and the residue was crystallized from hexane. The precipitate was filtered off and dried, yielding 7.4 g (24.6%) of 2-chloro-1-[3-(cyclopentyloxy)-4-methoxyphenyl]ethanone (interm. 1).

b) Sodium bis(trimethylsilyl)amide (5 ml) was added to a solution of 1,3-dihydro-2H-imidazol-2-one (0.84 g) in N,N-dimethylformamide (50 ml), stirred under a $N_2$ flow and cooled in an ice-bath. The reaction mixture was stirred for 30 minutes.

Intermediate 1 (2.69 g) was added portionwise and the resulting reaction mixture was stirred for 16 hours at RT, then for 2 hours at 50° C. The reaction mixture was stirred in methyl isobutyl ketone/water (200 ml/50 ml). The solvent was evaporated and methyl isobutyl ketone (100 ml) was added and azeotroped on the rotary evaporator. The mixture was purified by column chromatography over silica gel (eluent: $CH_2Cl_2/(CH_3OH/NH_3)$ 97/3). The desired fractions were collected and the solvent was evaporated. The white solid was stirred in DIPE, filtered off, washed with DIPE and dried, yielding 0.4 g (12.6%) of 1-[2-[3-(cyclopentyloxy)-4methoxyphenyl]-2-oxoethyl]-1,3-dihydro-2H-imidazol-2-one (interm. 2; mp. 201.1° C.).

c) A mixture of intermediate 2 (1 g) in THF (50 ml) was stirred under a $N_2$ flow at −78° C. Phenyllithium (3.52 ml; 1.8 M solution in cyclohexane/ether 70/30) was added dropwise and the mixture was stirred for 30 min at −78° C. The mixture was allowed to warm to RT and stirring was continued for one hour. More phenyllithium (1.5 ml) was added dropwise at RT and the mixture was stirred for another 2 hours. The reaction mixture was stirred and refluxed for 1 hour, then cooled on an ice-bath and quenched with a saturated $NH_4Cl$ solution. This mixture was extracted three times with $CH_2Cl_2$ (100 ml). The separated organic layer was dried over $MgSO_4$, filtered and the solvent was evaporated. The residue was purified by short column chromatography over silica gel (eluent: $CH_2Cl_2/CH_3OH/$ $(CH_3OH/NH_3)$ 90/5/5). The pure fractions were collected and the solvent was evaporated. The residue was triturated in DIPE. The precipitate was filtered off, washed with DIPE and dried, yielding 0.2 g (16%) of (±)-1-[2-[3-(cyclopentyloxy)-4-methoxyphenyl]-2-hydroxy-2-phenylethyl]-1,3-dihydro-2H-imidazol-2-one (interm. 3).

EXAMPLE A.2 a) A solution of 1-(diphenylmethyl)-2-imidazolidinone (10 g) and sodium hydroxide (100 mg) in methanol (50 ml) and formol (50 ml; 37%) was stirred at RT for 6 hours. The solvent was evaporated and the residue was taken up in water and extracted 3 times with $CHCl_3$. The separated organic layer was dried ($MgSO_4$), filtered and the solvent was evaporated. The residue was stirred in ether, filtered off and dried, yielding 9.7 g (86.6%) of product. A sample (2.5 g) was recrystallized from ethylacetate. The precipitate was filtered off and dried, yielding 0.49 g of 1-(diphenylmethyl)-3-(hydroxy-methyl)-2-imidazolidinone (interm. 4; mp. 133.5° C.).

b) A mixture of intermediate 4 (8.4 g) and triphenylphosphonium bromide (10.3 g) in acetonitrile (100 ml) was stirred and refluxed for 1 hour. The solvent was evaporated and the residue was taken up in toluene and boiled. The precipitate was filtered off and dried, yielding 17.5 g (96.2%) of triphenyl[3-(diphenylmethyl)-2, 3-dihydro-2-oxo-1H-imidazole-1-methyl] phosphonium bromide (interm. 5).

EXAMPLE A.3 a) A Grignard complex was formed with bromobenzene (18.84 g), magnesium, turnings (2.9 g), iodine (catalytic amount) and aluminum (catalytic amount) in THF (105 ml). A solution of bromobenzene in THF (100 ml) was added dropwise, under $N_2$ flow, to a stirs solution of magnesium, turnings and iodine in THF (5 ml). The reaction mixture was stirred and heated. After all bromobenzene was added, the reaction mixture was stirred and refluxed for 1 hour. The mixture was cooled on an ice-bath. A solution of 3-(cyclopentyloxy)-4-methoxybenzaldehyde (22.03 g) in THF (80 ml) was added dropwise at 0° C. The reaction mixture was stirred for 2 hours at RT, then cooled to 0° C. A saturated $NH_4Cl$ solution (200 ml) was added dropwise and this mixture was extracted twice with $CH_2Cl_2$ (100 ml). The separated organic layer was dried ($MgSO_4$), filtered and the solvent evaporated, yielding 29.3 g (98%) of (±)-3-(cyclopentyloxy)-4-methoxy-α-phenylbenzenemethanol (interm. 6).

b) A mixture of intermediate 6 (29.3 g) and manganese (IV) oxide (85 g) in $CH_2Cl_2$ (300 ml) was stirred for 48 hours at RT. The reaction mixture was filtered over dicalite and the filtrate was evaporated. The residue was crystallized from DIPE. The precipitate was filtered off, washed with DIPE, then dried, yielding 14 g (48%) of [3-(cyclopentyloxy)-4-methoxyphenyl] phenylmethanone (interm. 7; mp. 76.4° C.).

EXAMPLE A.4 a) A solution of sodium bis(trimethylsilyl)amide in THF (55 ml; 2M) was added to a mixture of ethyl 2-oxo-imidazolidine-1-carboxylate (1.58 g) in THF (150 ml) which was stirred at RT. Stirring was continued for 1 hour. The mixture was cooled and 2-bromo-1-(3,4-dimethoxyphenyl)ethanone (2.6 g) in THF (50 ml) was added. The mixture was stirred for 1 hour and decomposed with water. The aqueous layer was extracted with $CH_2Cl_2$, and the organic layer was dried ($MgSO_4$), filtered off and evaporated. The residue was purified by column chromatography over silica gel (eluent: $CH_2Cl_2/CH_3OH$ 98/2). The pure fractions were collected and their solvent evaporated. The residue was crystallized from ethylacetate, filtered off and dried, yielding 1.57 g (46.7%) of ethyl 3-[2-(3,4-dimethoxyphenyl)-2-oxoethyl]-2-oxo-1-imidazolidine-1-carboxylate (interm. 8; mp. 133.9° C.).

b) A mixture of intermediate 8 (0.5 g) and potassium carbonate (0.5 g) in ethanol (50 ml) was stirred and refluxed for 30 minutes, then cooled, poured out into water and extracted three times with $CH_2Cl_2$. The organic layer was separated and the solvent evaporated. The residue was purified by column chromatography over silica gel (eluent: $CH_2Cl_2/CH_3OH$ 95/5). The pure fractions were collected and the solvent was evaporated. The residue was crystallized from $CH_3CN$. The precipitate was filtered off and dried, yielding 1.62 g (37.5%) of 1-[2-(3,4-dimethoxyphenyl)-2-oxoethyl]-2-imidazolidinone (interm. 9; mp. 166.6° C.).

c) (±)-1-[2-(3,4-dimethoxyphenyl)-2-hydroxy-2-phenylethyl]-2-imidazolidinone (interm. 10; mp. 154.4° C.) was prepared according to the procedure described in example A.1.c.

B. Preparation of the compounds of formula (I)

EXAMPLE B.1 procedure 1 a) Thionylchloride (0.5 g) was added dropwise to a solution of intermediate 3 (1 g) in $CH_2Cl_2$ (10 ml) at RT. The reaction mixture was stirred at 30° C. for 3 hours after which the solvent was evaporated. The residue was co-evaporated with toluene and the residual mixture was taken up in dichloromethane and washed with $K_2CO_3$ (10% solution). The organic layer was dried over $MgSO_4$, filtered and concentrated under reduced pressure yielding 0.8 g of the crude 1-[2-[3-cyclopentyloxy)-4-methoxyphenyl]ethenyl]-1,3-dihydro-2H-imidazolone (compound 1; E/Z isomer ratio=60/40).

b) Compound (1) was further purificied and separated into its pure E and Z isomer on a silicagel column (eluent: $CH_2Cl_2$/MeOH 98/2) yielding 50 mg of E-1-[2-[3-cyclopentyloxy) -4methoxyphenyl]ethenyl]-1,3-dihydro-2H-imidazolone (comp. 2) and 50 mg of Z-1-[2-[3-cyclopentyloxy)-4-methoxyphenyl]ethenyl]1,3-dihydro-2H-imidazolone (comp. 3).

procedure 2

A solution of intermediate 3 (1 g) and triethylsilane (1 ml) in $CH_2Cl_2$ (100 ml) was stirred at 0–3° C. A solution of trifluoroacetic acid (0.68 ml) in $CH_2Cl_2$ (50 ml) was added dropwise over 2 hours. The resulting reaction mixture was allowed to warm to RT, then stirred for 48 hours. The solution was neutralized with solid $Na_2CO_3$, filtered, and the filtrate was evaporated. The residue was purified over silica gel on a glass filter (eluent: $CH_2Cl_2/CH_3OH$ 90/10). The pure fractions were collected and the solvent was evaporated. The residue was crystallized from $CH_3CN$. The precipitate was filtered off, washed with $CH_3CN$, DIPE, then dried, yielding 0.4 g (41.6%) of (E)-1-[2-[3-(cyclopentyloxy)-4-methoxyphenyl]-2-phenylethenyl]-1,3-dihydro-2H-imidazol-2-one (comp. 2).

EXAMPLE B.2 a) A mixture of sodium hydride (2.88 g; 50%) in THF (250 ml) was stirred at RT under $N_2$ flow. Ethyl (diethylphosphono)acetate (13.45 g) was added dropwise while keeping the temperature below 15° C. The reaction mixture was stirred for 30 minutes. Intermediate 2 (6.32 g) was added portionwise. Stirring was continued for 1 hour. The reaction mixture was cooled on an ice bath and decomposed with a $NH_4Cl$ solution. The aqueous layer was extracted 3 times with $CH_2Cl_2$. The separated organic layer was dried ($MgSO_4$), filtered and the solvent was evaporated. The residue was purified by column chromatography over silica gel (eluent: $CH_2C_2/C_2H_5OH$ 95/5). The pure factions were collected and the solvent was evaporated. The residue was crystallized from $CH_3CN$. The precipitate was filtered off and dried, yielding 1.19 g (15.4%) of ethyl (E)-3-(cyclopentyloxy)-β-[(2,3dihydro-2-oxo-1H-imidazol-1-yl)methylene]-4methoxybenzene-propanoate (comp. 4; mp. 164.1° C.). The filtrate was evaporated, yielding 10 g of ethyl (Z)-3-(cyclopentyloxy)-β-[(2,3-dihydro-2-oxo-1H-imidazol-1-yl)methylene]4-methoxy-benzenepropanoate (comp. 5).

In an analogous way was prepared:

(E)-3,4-dimethoxy-β[(2-oxo-1-imidazolidinyl) methylene]benzenepropanenitrile (comp. 6)

b) A mixture of compound 5 (10 g) in ethanol (50 ml) was stirred at RT. Sodium hydroxide (50 ml; 1N) was added dropwise. Stirring was continued for 16 hours. The solvent was evaporated and the residue was taken up in water and washed 3 times with $CH_2Cl_2$. The aqueous layer was acidified with HCl 1N and extracted 3 times with $CH_2Cl_2$. The organic layer was separated, dried ($MgSO_4$), filtered and the solvent was evaporated. The residue was purified by column chromatography over silica gel (eluent: $CH_2Cl_2/CH_3OH$ 95/5). The pure fractions were collected and the solvent was evaporated. The residue was crystallized from $CH_3CN$. The precipitate was filtered off and dried, yielding 2.2 g (36.1%) of (Z)-3-(cyclopentyloxy)-β-[(2,3-dihydro-2-oxo-1H-imidazol-1-yl)methylene]4-methoxybenzenepropanoic acid (comp. 7; mp. 193.7° C.).

EXAMPLE B.3

A mixture of intermediate 10 (2.04 g) in THF (120 ml) and hydrochloric acid (6 ml; 1N) was stirred and refluxed for 8 hours. The reaction mixture was cooled, basified with a $K_2CO_3$ solution and the solvent was evaporated. The residue was taken up in water and extracted with $CH_2Cl_2$. The separated organic layer was dried ($MgSO_4$), filtered and the solvent was evaporated. The residue was purified by column chromatography over silica gel (eluent: (0.5% ammonium acetate in $H_2O$)/$CH_3CN$ 99.5/0.5). The desired fraction was collected and the solvent was evaporated. The residue was stirred in DIPE, filtered off and dried, yielding 0.38 g (11.7%) of 1-[2-(3,4-dimethoxyphenyl)-2-phenylethenyl]-2-imidazolidinone (comp. 8; mp. 155.3° C.).

EXAMPLE B.4

A mixture of intermediate 10 (2 g) in acetic anhydride (20 ml) was stirred and refluxed for 6 hours. The solvent was evaporated and toluene was added twice and evaporated again. The residue was purified by column chromatography over silica gel (eluent: $CH_2Cl_2/CH_3OH$ 98/2). The pure fractions were collected and the solvent was evaporated, yielding 1.2 g of product. This fraction was purified by HPLC over silica gel (eluent: $CH_2Cl_{2/CH_3}OH$ 98/2). The pure fractions were collected and the solvent was evaporated, yielding 1.02 g of product. This fraction was crystallized from ethyl acetate. The precipitate was filtered off and dried, yielding 0.53 g (24.8%) of 1-acetyl-3-[2-(3, 4dimethoxyphenyl)-2-phenylethenyl]-2-imidazolidinone (comp. 9).

EXAMPLE B.5

THF (200 ml) was stirred at RT under $N_2$ flow. Sodium hydride (0.84 g; 50%) was added. Intermediate 5 (6.05 g) was added portionwise. Stirring was continued for 2.5 hours. Intermediate 7 (2.96 g) was added and the reaction mixture was stirred for 16 hours. The mixture was cooled on an ice-bath and decomposed with an aqueous $NH_4Cl$ solution, then extracted 3 times with diethyl ether. The separated organic layer was dried ($MgSO_4$), filtered, and the solvent was evaporated. The residue was purified by column chromatography over silica gel (eluent: $CH_2Cl_2/CH_3OH$ 99/1). The desired fractions were collected and the solvent was evaporated, yielding 6 g of product. This fraction was purified by column chromatography over silica gel (eluent: $CH_2Cl_2/CH_3OH$ 99.9/0.1). The desired fraction groups were collected and their solvent was evaporated, yielding 1.2 g fraction 1 and 1.1 g of fraction 2. Fraction 1 was stirred in DIPE, filtered off, and dried, yielding 0.82 g (15%) of (E)-1-[2-[3-(cyclopentyloxy)-4-methoxyphenyl]-2-phenylethenyl]-3-(diphenylmethyl)-1,3dihydro-2H-imidazol-2-one (comp. 10). Fraction 2 was stirred in DIPE, filtered off, and dried, yielding 0.57 g (10.5%) of (Z)-1-[2-[3-(cyclopentyloxy)-4-methoxyphenyl]-2-phenylethenyl]-3-(diphenylmethyl)-1,3-dihydro-2H-imidazol-2-one (comp. 11).

In an analogous way were prepared:

(Z)-1-[2-[3-(cyclopentyloxy)-4-methoxyphenyl]-1-propenyl]-3-(diphenylmethyl)-2H-imidazol-2-one (comp. 12);

(E)-1-[2-[3-(cyclopentyloxy)-4-methoxyphenyl]-1-propenyl]-3-(diphenylmethyl)-2H-imidazol-2-one (comp. 13).

C. Pharmacological example

EXAMPLE C.1

Inhibition of recombinant human mononuclear lymphocyte (MNL) phosphodiesterase type IV B produced in insect cells with a baculovirus vector, The alleviating and/or curing effect of the instant compounds on allergic and atopic diseases was assessed by an in vitro assay system to detect an inhibiting effect on the recombinant human MNL phosphodiesterase type IV B.

Seventy-two hours after infection with recombinant baculovirus, the insect cells were harvested and pelleted at 500 g for 5 minutes. The cells were lysed in 10 ml lysis-buffer consisting of 20 mM Tris, 10 mM EGTA, 2 mM $Na_2EDTA$, 1% Triton-X-100, 1 mM $Na_3VO_4$, 10 mM NaF, 2 μg/ml of leupeptine, pepstatine and aprotinine, 0.3 μg/ml benzamidine and 100 μg/ml TPCK pH 7.5. After 5 minutes on ice, solubilized cells were centrifuged at 4000 rpm for 15 minutes at 4° C. The resulting supernatant was filtered through a 0.45 μm filter (Millipore) and brought to TBS buffer (50 mM Tris, 150 mM NaCl pH 7.4).

The supernatant containing phosphodiesterase (PDE) type IV B, was subsequently loaded onto a 5 ml anti-FLAG-$M_2$ affinity gel column, previously activated with 5 ml 100 mM glycine pH 3.5 and equilibrated with 20 ml 50 mM Tris, 150 mM NaCl pH 7.4. After washing the column with equilibration buffer, PDE IV was eluted in 1.5 ml fractions containing 37.5 μl 1M Tris pH 8. The fractions were dialyzed overnight against 20 mM Tris, 2 mM $Na_2EDTA$ and 400 mM NaCl pH 7.5 and tested for PDE IV activity. Indentification was done on SDS PAGE and Western Blot (anti-FLAG-$M_2$). Active fractions were pooled, brought to 10% glycerol and stored at −70° C.

The incubation mixture (pH 8) (200 μl) contained 20 mM Tris, 10 mM magnesium sulphate, 0.8 μM $^3$H-cAMP (310 mCi/mmole) and the phosphodiesterase type IV, the amount depending on the enzymatic activity. A protein concentration was chosen that showed a linear increase of phosphodiesterase activity during an incubation period of maximum 10 minutes at 37° C. and where less than 10% of the initial substrate was hydrolyzed.

When the effect of different compounds on phosphodiesterase activity was tested, the medium without cAMP was incubated with the compound(s) or its carrier (DMSO—1% final concentration) for 5 min. The enzymatic reaction was started by addition of $^3$H-cAMP and stopped 10 min later after transferring the microtiter-plate in a waterbath at 100° C. for 5 min. After cooling to room temperature, alkaline phosphatase (0.25 μg/ml) was added and the mixture was incubated at 37° C. for 20 min. 100 μl of the mixture was subsequently applied to a GF-B filter-microtiter-plate (Millipore) filled with 300 μl DEAE-Sephadex-A25 suspension. The plate was washed 3 times with 75 μl 20 mM Tris pH 7.5 and the filtrates were collected for counting in the Packard Top Count scintillation counter.

The inhibiting effect of the present compounds on recombinant human MNL phosphodiesterase PDE IV B was measured at different concentrations of the instant compounds. The $IC_{50}$ values (expressed in M) were calculated graphically from the thus obtained inhibition values. Compound Nos. 2, 4 and 12 had an $IC_{50}$ value lower than $1 \times 10^{-6}$ M. The other compounds had an $IC_{50}$ value higher than or equal to $1 \times 10^{-6}$ M.

EXAMPLE C.2

Dextran-induced oedema formation in mouse ear.

Systemic injection of dextran T500 in normal, non-sensitized mice elicits increased vascular permeability, leading to extravasation and oedema of the extremities. When dextran is injected together with a blue dye, blueing of the ears is the most prominent feature of oedematous response.

Male Swiss mice weighing 24–26 g were orally pretreated with the test compound dissolved in PEG-200 at different concentrations or solvent. One hour later, the mice were given an intravenous injection with an isotonic saline solution containing 12 mg/ml dextran T500 and 2.6 mg/ml pontamine sky-blue dye, in a volume of 0.1 ml per 10 g body weight. One hour and forty-five minutes later, the animals are sacrificed by ether and their ears removed. Extraction and quantification of the extravasated dye is done as described by Van Wauwe and Goossens (Drug Dev. Res. 1986, 8, 213–218).

The extravasation of the dye is characterized by the blueing value which is defined as the concentration of the extracted dye in both ears. The background blueing value was determined once as the mean blueing value obtained by injecting a group of mice with a saline solution containing only dextran T500 and the blue dye. Table 1 lists the percentage inhibition of the extravasation of the dye when compared with the background extravasation of the dye when the test compound was administered at a dose of 5 mg/kg.

TABLE 1

| Compound Number | % inhibition |
| --- | --- |
| 2 | 15.5 |
| 4 | 25.9 |
| 7 | 49.9 |
| 8 | 17.9 |
| 9 | 11.1 |
| 10 | 40.1 |
| 11 | 19.3 |

D. Composition examples

The following formulations exemplify typical pharmaceutical compositions suitable for systemic or topical administration to animal and human subjects in accordance with the present invention.

"Active ingredient" (A.I.) as used throughout these examples relates to a compound of formula (I) or a pharmaceutically acceptable addition salt thereof.

EXAMPLE D.1 film-coated tablets

Preparation of tablet core

A mixture of 100 g of the A.I., 570 g lactose and 200 g starch was mixed well and thereafter humidified with a solution of 5 g sodium dodecyl sulfate and 10 g polyvinylpyrrolidone in about 200 ml of water. The wet powder mixture was sieved, dried and sieved again. Then there was added 100 g microcrystalline cellulose and 15 g hydrogenated vegetable oil. The whole was mixed well and compressed into tablets, giving 10,000 tablets, each comprising 10 mg of the active ingredient.

Coating

To a solution of 10 g methyl cellulose in 75 ml of denaturated ethanol there was added a solution of 5 g of ethyl cellulose in 150 ml of dichloromethane. Then there were added 75 ml of dichloromethane and 2.5 ml 1,2,3-propanetriol. 10 g of polyethylene glycol was molten and dissolved in 75 ml of dichloromethane. The latter solution was added to the former and then there were added 2.5 g of magnesium octadecanoate, 5 g of polyvinylpyrrolidone and 30 ml of concentrated color suspension and the whole was homogenated. The tablet cores were coated with the thus obtained mixture in a coating apparatus.

EXAMPLE D.2

2% cream 75 mg stearyl alcohol, 2 mg cetyl alcohol, 20 mg sorbitan monostearate and 10 mg isopropyl myristate are introduced into a doublewall jacketed vessel and heated until the mixture has completely molten. This mixture is added to a separately prepared mixture of purified water, 200 mg propylene glycol and 15 mg polysorbate 60 having a temperature of 70 to 75° C. while using a homogenizer for liquids. The resulting emulsion is allowed to cool to below 25° C. while continuously mixing. A solution of 20 mg A.I., 1 mg polysorbate 80 and purified water and a solution of 2 mg sodium sulfite anhydrous in purified water are next added to the emulsion while continuously mixing. The cream, 1 g of the A.I. is homogenized and filled into suitable tubes.

EXAMPLE D.3

2% topical gel

To a solution of 200 mg hydroxypropyl β-cyclodextrine in purified water is added 20 mg of A.I. while stirring. Hydrochloric acid is added until complete dissolution and then sodium hydroxide is added until pH 6.0. This solution is added to a dispersion of 10 mg carrageenan PJ in 50 mg propylene glycol while mixing. While mixing slowly, the mixture is heated to 50° C. and allowed to cool to about 35° C. whereupon 50 mg ethyl alcohol 95% (v/v) is added. The rest of the purified water q.s. ad 1 g is added and the mixture is mixed to homogenous.

EXAMPLE D.4

2% topical cream

To a solution of 200 mg hydroxypropyl β-cyclodextrine in purified water is added 20 mg of A.I. while stirring. Hydrochloric acid is added until complete dissolution and next sodium hydroxide is added until pH 6.0. While stirring, 50 mg glycerol and 35 mg polysorbate 60 are added and the mixture is heated to 70° C. The resulting mixture is added to a mixture of 100 mg mineral oil, 20 mg stearyl alcohol, 20 mg cetyl alcohol, 20 mg glycerol monostearate and 15 mg sorbate 60 having a temperate of 70° C. while mixing slowly. After cooling down to below 25° C., the rest of the purified water q.s. ad 1 g is added and the mixture is mixed to homogenous.

EXAMPLE D.5

2% liposome formulation

A mixture of 10 g phosphatidyl choline and 1 g cholesterol in 7.5 g ethyl alcohol is stirred and heated at 40° C. until complete dissolution. 2 g A.I. microfine is dissolved in purified water by mixing while heating at 40° C. The alcoholic solution is added slowly to the aqueous solution while homogenizing during 10 minutes. 1.5 g Hydroxypropyl-methylcellulose in purified water is added while mixing until swelling is complete. The resulting solution is adjusted to pH 5.0 with sodium hydroxide 1 N and diluted with the rest of the purified water ad 100 g.

We claim:
1. A compound of formula

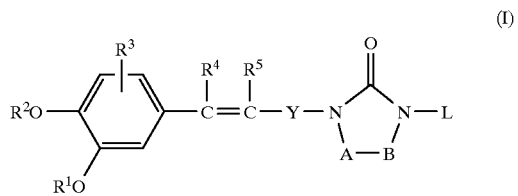

a N-oxide form, a pharmaceutically acceptable acid or base addition salt or a stereochemically isomeric form thereof, wherein:

$R^1$ and $R^2$ each independently are hydrogen; $C_{1-6}$alkyl; difluoromethyl; trifluoromethyl; $C_{3-6}$cycloalkyl; a saturated 5-, 6- or 7-membered heterocycle containing one or two heteroatoms selected from oxygen, sulfur or nitrogen; indanyl; bicyclo[2.2.1]-2-heptenyl; bicyclo [2.2.1]heptanyl; $C_{1-6}$alkylsulfonyl; arylsulfonyl; or $C_{1-10}$alkyl substituted with one or two substituents each independently selected from aryl, pyridinyl, thienyl, furanyl, $C_{3-7}$cycloalkyl and a saturated 5-, 6- or 7-membered heterocycle containing one or two heteroatoms selected from oxygen, sulfur or nitrogen;

$R^3$ is hydrogen, halo or $C_{1-6}$alkyloxy;

$R^4$ is hydrogen; cyano; $C_{1-6}$alkyl; $C_{1-6}$alkyloxycarbonyl; aryl or $C_{1-6}$alkyl substituted with aryl, cyano, carboxyl or $C_{1-6}$alkyloxycarbonyl;

$R^5$ is hydrogen; cyano; $C_{1-6}$alkyl; $C_{1-6}$alkyloxycarbonyl; aryl or $C_{1-6}$alkyl substituted with aryl, cyano, carboxyl or $C_{1-6}$alkyloxycarbonyl;

Y is a direct bond or $C_{1-3}$alkanediyl;

—A—B— is a bivalent radical of formula:
—$CR^6$=$CR^7$— (a-1); or
—$CHR^6$—$CHR^7$— (a-2);

wherein each $R^6$ and $R^7$ independently is hydrogen or $C_{1-4}$alkyl;

L is hydrogen; $C_{1-6}$alkyl; $C_{1-6}$alkylcarbonyl; $C_{1-6}$alkyloxycarbonyl; $C_{1-6}$alkyl substituted with one or two substituents selected from the group consisting of hydroxy, $C_{1-4}$alkyloxy, $C_{1-4}$alkyloxycarbonyl, mono- and di($C_{1-4}$alkyl)amino, aryl and Het; $C_{3-6}$alkenyl; $C_{3-6}$alkenyl substituted with aryl; piperidinyl; piperidinyl substituted with $C_{1-4}$alkyl or aryl$C_{1-4}$alkyl; $C_{1-6}$alkylsulfonyl or arylsulfonyl;

aryl is phenyl or phenyl substituted with one, two or three substituents selected from halo, hydroxy, $C_{1-4}$alkyl, $C_{1-4}$alkyloxy, $C_{3-6}$cycloalkyl, trifluoromethyl, amino, nitro, carboxyl, $C_{1-4}$alkyloxycarbonyl and $C_{1-4}$alkylcarbonylamino;

Het is morpholinyl; piperidinyl; piperidinyl substituted with $C_{1-4}$alkyl or aryl$C_{1-4}$alkyl; piperazinyl; piperazinyl substituted with $C_{1-4}$alkyl or aryl$C_{1-4}$alkyl; pyridinyl; pyridinyl substituted with $C_{1-4}$alkyl; furanyl; furanyl substituted with $C_{1-4}$alkyl; thienyl or thienyl substituted with $C_{1-4}$alkyl or $C_{1-4}$alkylcarbonylamino.

2. A compound according to claim 1 wherein:

$R^1$ and $R^2$ each independently are hydrogen, $C_{1-6}$alkyl, difluoromethyl, trifluoromethyl, $C_{3-6}$cycloalkyl or bicyclo[2.2.1]-2-heptenyl;

$R^4$ is hydrogen, cyano, $C_{1-6}$alkyl, $C_{1-6}$alkyloxycarbonyl, aryl or aryl$C_{1-6}$alkyl;

$R^5$ is hydrogen, cyano, $C_{1-6}$alkyl, $C_{1-6}$alkyloxycarbonyl, aryl or aryl$C_{1-6}$yl;

L is hydrogen; $C_{1-6}$alkyl; $C_{1-6}$alkyl substituted with hydroxy, $C_{1-4}$alkyloxy, $C_{1-4}$alkyloxycarbonyl, mono- or di($C_{1-4}$alkyl)amino, aryl or Het; $C_{3-6}$alkenyl; $C_{3-6}$alkenyl substituted with aryl; piperidinyl; piperidinyl substituted with $C_{1-4}$alkyl or aryl$C_{1-4}$alkyl; $C_{1-6}$alkylsulfonyl or arylsulfonyl;

aryl is phenyl or phenyl substituted with one, two or three substituents selected from halo, $C_{1-4}$alkyl, $C_{1-4}$alkyloxy, $C_{3-6}$cycloalkyl, trifluoromethyl, amino and $C_{1-4}$alkylcarbonylamino.

3. A compound according to claim 1 wherein $R^4$ is cyano; $C_{1-6}$alkyl; aryl or $C_{1-6}$alkyl substituted with aryl, cyano, carboxyl or $C_{1-6}$alkyloxycarbonyl; or $R^5$ is cyano; $C_{1-6}$alkyl; aryl or $C_{1-6}$alkyl substituted with aryl, cyano, carboxyl or $C_{1-6}$alkyloxycarbonyl.

4. A compound according to claim 1 wherein $R^1$ is hydrogen; a saturated 5-, 6- or 7-membered heterocycle containing one or two heteroatoms selected from oxygen, sulfur or nitrogen; bicyclo[2.2.1]-2-heptenyl; $C_{1-6}$alkylsulfonyl; arylsulfonyl; or $C_{1-10}$alkyl substituted with one or two substituents each independently selected from pyridinyl, thienyl, furanyl, $C_{3-7}$cycloalkyl and a saturated 5-, 6- or 7-membered heterocycle containing one or two heteroatoms selected from oxygen, sulfur or nitrogen.

5. A compound according to claim 1 wherein $R^4$ is aryl or $C_{1-6}$alkyl substituted with aryl, cyano, carboxyl or $C_{1-6}$alkyloxycarbonyl; or $R^5$ is aryl or $C_{1-6}$alkyl substituted with aryl, cyano, carboxyl or $C_{1-6}$alkyloxycarbonyl.

6. A compound according to claim 1 wherein $R^1$ is hydrogen; $C_{1-6}$alkyl; difluoromethyl; trifluoromethyl; a saturated 5-, 6- or 7-membered heterocycle containing one or two heteroatoms selected from oxygen, sulfur or nitrogen; indanyl; bicyclo[2.2.1]-2-heptenyl; bicyclo[2.2.1]heptanyl; $C_{1-6}$alkylsulfonyl; arylsulfonyl; or $C_{1-10}$alkyl substituted with one or two substituents each independently selected from aryl, pyridinyl, thienyl, furanyl, $C_{3-7}$cycloalkyl and a saturated 5-, 6- or 7-membered heterocycle containing one or two heteroatoms selected from oxygen, sulfur or nitrogen.

7. A compound according to claim 1 wherein $R^4$ is hydrogen; cyano; $C_{1-6}$alkyl; $C_{1-6}$alkyloxycarbonyl or $C_{1-6}$alkyl substituted with cyano, carboxyl or $C_{1-6}$alkyloxycarbonyl; or $R^5$ is hydrogen; cyano; $C_{1-6}$alkyl; $C_{1-6}$alkyloxycarbonyl or $C_{1-6}$alkyl substituted with cyano, carboxyl or $C_{1-6}$alkyloxycarbonyl.

8. A compound according to claim 1 wherein $R^1$ is hydrogen; a saturated 5-, 6- or 7-membered heterocycle containing one or two heteroatoms selected from oxygen, sulfur or nitrogen; indanyl; bicyclo[2.2.1]-2-heptenyl; bicyclo[2.2.1]heptanyl; $C_{1-6}$alkylsulfonyl; arylsulfonyl; or $C_{1-10}$alkyl substituted with one or two substituents each independently selected from aryl, pyridinyl, thienyl, furanyl, $C_{3-7}$cycloalkyl and a saturated 5-, 6- or 7-membered heterocycle containing one or two heteroatoms selected from oxygen, sulfur or nitrogen.

9. A compound according to claim 1 wherein $R^4$ is $C_{1-6}$alkyl substituted with cyano, carboxyl or $C_{1-6}$alkyloxycarbonyl; or $R^5$ is $C_{1-6}$alkyl substituted with cyano, carboxyl or $C_{1-6}$alkyloxycarbonyl.

10. A compound according to claim 1 wherein $R^1$ is hydrogen; a saturated 5-, 6- or 7-membered heterocycle containing one or two heteroatoms selected from oxygen, sulfur or nitrogen; bicyclo[2.2.1]-2-heptenyl; $C_{1-6}$alkylsulfonyl; arylsulfonyl; or $C_{1-10}$alkyl substituted with one or two substituents each independently selected from pyridinyl, thienyl, furanyl, $C_{3-7}$cycloalkyl and a saturated 5-, 6- or 7-membered heterocycle containing one or two heteroatoms selected from oxygen, sulfur or nitrogen.

11. A compound according to claim 1 or 2 wherein $R^1$ is $C_{1-6}$alkyl or $C_{3-6}$cycloalkyl and $R^2$ is $C_{1-6}$alkyl.

12. A compound according to claim 1, 2 or 11 wherein $R^3$ is hydrogen.

13. A compound according to claim 1, 2, 11 or 12 wherein Y is a direct bond, methylene or 1,2-ethanediyl.

14. A compound according to claim 1 or 2, or according to any one of claims 11 to 13 wherein L is hydrogen or $C_{1-6}$alkyl.

15. A compound according to claim 1 or 2, or according to any one of claims 11 to 14 wherein —A—B— is a bivalent radical of formula (a-1) wherein $R^6$ and $R^7$ are both hydrogen.

16. A compound according to claim 1, wherein the compound is:

1-[2-[3-(cyclopentyloxy)-4-methoxyphenyl]-2-phenylethenyl]-1,3-dihydro2H-imidazol-2-one;

ethyl 3-(cyclopentyloxy)-β-[(2,3-dihydro-2-oxo-1H-imidazol-1-yl)methylene]4-methoxybenzenepropanoate;

1-[2-[3-(cyclopentyloxy)-4-methoxyphenyl]-1-propenyl]-3-(diphenylmethyl)-2H-imidazol-2-one;

their N-oxide forms, their pharmaceutically acceptable acid or base addition salts and their stereoisomeric forms.

17. A composition comprising a pharmaceutically acceptable carrier and, as active ingredient, a therapeutically effective amount of a compound as claimed in any one of claims 1 to 16.

18. A process of preparing a composition as claimed in claim 17, wherein a pharmaceutically acceptable carrier is intimately mixed with a therapeutically effective amount of a compound as described in any one of claims 1 to 16.

19. A method of treating allergic, atopic or inflammatory diseases in warm blooded animals which comprises administering to an animal in need of such treatment an effective amount of a compound according to any one of claims 1 to 16.

20. A method of treating atopic dermatitis in warm blooded animals which comprises administering to an animal in need of such treatment an effective amount of a compound according to any one of claims 1 to 16.

* * * * *